United States Patent [19]
Yamaguchi et al.

[11] Patent Number: 5,278,413
[45] Date of Patent: * Jan. 11, 1994

[54] INFRARED MICROSCOPIC SPECTROMETER

[75] Inventors: Tetsuji Yamaguchi, Kyoto; Juichiro Ukon, Ibaraki; Kazuyuki Ikemoto, Uji, all of Japan

[73] Assignee: Horiba, Ltd., Kyoto, Japan

[*] Notice: The portion of the term of this patent subsequent to Jul. 20, 2010 has been disclaimed.

[21] Appl. No.: 821,746

[22] Filed: Jan. 13, 1992

[30] Foreign Application Priority Data

Jan. 16, 1991 [JP] Japan .................. 3-15767

[51] Int. Cl.$^5$ .......................... G01N 21/01; G01J 3/45
[52] U.S. Cl. ..................................... 250/347; 250/339
[58] Field of Search .............. 250/339, 343, 347, 353, 250/341, 360.1; 356/244, 346

[56] References Cited

U.S. PATENT DOCUMENTS

| | | | |
|---|---|---|---|
| Re. 32,912 | 4/1989 | Doyle | 356/244 |
| 3,645,631 | 2/1972 | Gupta | 250/341 X |
| 4,547,068 | 10/1985 | Covey et al. | 356/244 |
| 4,594,509 | 6/1986 | Simon et al. | 250/338.1 |
| 4,657,390 | 4/1987 | Doyle | 356/346 |
| 4,843,242 | 6/1989 | Doyle | 250/330 |
| 4,852,955 | 8/1989 | Doyle et al. | 350/1.2 |

FOREIGN PATENT DOCUMENTS

0116321 1/1984 Fed. Rep. of Germany.

OTHER PUBLICATIONS

Patent Abstracts of Japan, P-1134, Nov. 21, 1990, vol. 14/No. 530 Abstract of JP 2-223847.
Patent Abstracts of Japan, P-148, Oct. 14, 1982, vol. 6/No. 203 Abstract of JP 57-111435.

*Primary Examiner*—Constantine Hannaher
*Assistant Examiner*—Edward J. Glick
*Attorney, Agent, or Firm*—Price, Gess & Ubell

[57] ABSTRACT

An infrared microscopic spectrometer includes an optical system which allows for a shifting of the optical path interactive with a sample from a sample transmissive optical path to an optical path through an ATR crystal using ATR analysis. In the shown embodiment, the shift in the optical path is in a direction perpendicular to a transmissive optical axis, at least along a portion of the shift adjacent to the transmissive optical axis. The shift is undertaken by a moving means which moves the collecting element providing the infrared rays. A sample-holding structure allows the ATR crystal to be rotated or detachably removed, as necessary.

9 Claims, 7 Drawing Sheets

INFRARED MICROSCOPIC SPECTROMETER

FIELD OF THE INVENTION

The present invention relates to infrared microscopic spectrometers and, more particularly, to an optical arrangement for an infrared microscopic spectrometer which allows for attenuated total reflection (ATR) analysis.

BACKGROUND OF THE INVENTION

FIG. 6 shows a conventional infrared microscopic spectrometer. Therein, infrared rays from a source 1 are incident upon a sample 3 through a condenser mirror system 2. The condenser mirror system 2 may be a Cassegrain object mirror system.

The light transmitted through the sample 3 is enlargedly focused into an image by a second object mirror system 4, which may also be a Cassegrain object mirror system. The image projected by the second object mirror system 4 is projected into a spectrometric system 5 and sent to a display device 6 for the purposes of carrying out an analysis.

It is not possible to obtain a transmission spectrum with the system depicted in FIG. 6 when a sample has an extremely strong absorption coefficient. For such high absorption samples, an attenuated total reflection (ATR) analysis must be conducted.

FIG. 7 shows a rough schematic depiction of an ATR analysis. Therein, incident infrared light is collected by collecting mirror system 7 and reflected from flat mirror 9 into an ATR crystal 11. The ATR crystal 11 is a reflecting, highly refractive optical medium. It is constructed of highly refractive materials such as KRS-5, germanium, or silicon. The ATR crystal is arranged within the optical path formed between flat mirrors 9 and 10, and a sample 12 is placed on one surface of the ATR crystal in contact with the crystal 11.

The infrared rays which are incident upon the ATR crystal 11 are totally reflected, and the infrared rays having a specified wavelength are absorbed by an ingredient to be measured within the sample 12. The wavelength absorbed depends upon the inducing radical of the ingredient to be measured within the sample.

The infrared rays passing through the sample 12, and being totally reflected by the ATR crystal 11, exit the crystal 11. The rays are incident upon the spectrometer (not shown) through the flat mirror 10 and the collecting mirror system 8 in order to obtain an infrared spectrum corresponding to the ingredient to be measured.

As shown in FIG. 6, the infrared microscopic spectrometer requires that the condenser mirror system 2 and the object mirror system 4 be arranged along a singular optical axis so that the infrared rays from the light source 1 travelling through the sample 3 may be used to provide an infrared spectrum. On the other hand, in an infrared spectrometer using the ATR method of analysis, the infrared rays exiting the ATR crystal travel along a different optical axis from the incident rays from the light source. Thus, an ATR analysis cannot be undertaken by an infrared microscopic spectrometer as shown in FIG. 6, and it is necessary to use a different measurement apparatus, depending upon the sample to be measured.

An infrared microscopic spectrometer which incorporates an apparatus for ATR analysis is shown in FIG. 8. Therein, flat mirrors 15, 16, 17, and 18 and collecting mirrors 13 and 14 are configured and reconfigured to provide a requisite optical path flowing through the ATR crystal 11 every time the incident angle of the infrared rays is altered or the sample is exchanged.

OBJECTS OF THE INVENTION

It is therefore an object of the present invention to provide an infrared microscopic spectrometer which can easily incorporate both transmission and ATR analysis without realigning the optical elements along the optical path.

It is therefore a further object of the present invention to provide an infrared microscopic spectrometer which incorporates ATR analysis using a single apparatus which can be used to measure both low absorption coefficient samples and high absorption coefficient samples.

It is yet a still further object of the present invention to provide a simplified system for changing samples in an infrared spectrometer which can use both transmissive infrared spectrometry and ATR analysis.

SUMMARY OF THE INVENTION

The present invention provides a system within an infrared microscopic spectrometer for shifting an optical path interactive with a sample from a transmissive optical path to an optical path through an ATR crystal. The shift of the optical path is parallel to a direction perpendicular to a transmissive optical axis.

In the preferred embodiment, an infrared microscopic spectrometer includes a collecting element which focuses infrared rays upon a sample, an analysis portion which receives the infrared rays from the sample and spectrometrically analyzes the rays, and a moving means which shifts the collecting element with respect to the analysis portion.

In the shown embodiment, the moving means travels between a first position which allows transmissive infrared analysis and a second position which allows ATR analysis. The first position provides a singular optical axis directly aligning the collecting element, the sample, and the analysis portion. The moving means may then shift the collecting element along a direction perpendicular to the transmissive optical axis to provide an optical path which allows the infrared rays to travel through an ATR crystal for ATR analysis.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein.

Figure 1:
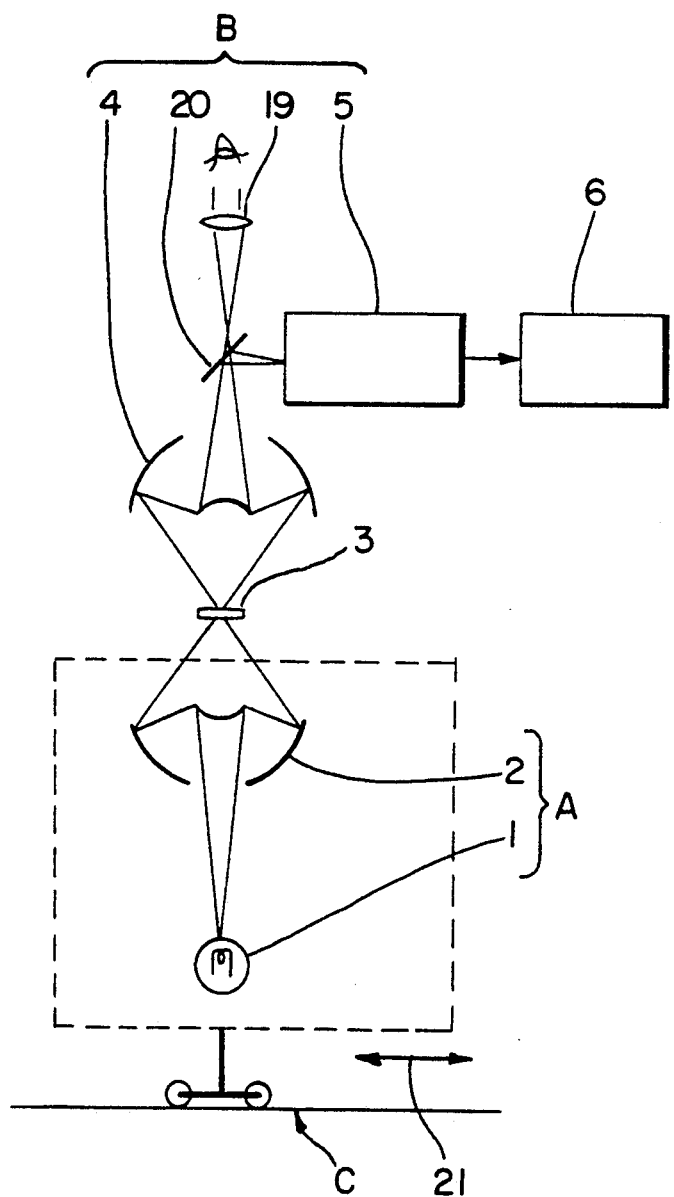
FIG. 1 is a cross-sectional depiction of an optical arrangement for transmission infrared microscopic spectrometry by the preferred embodiment of the invention.
Figure 2:
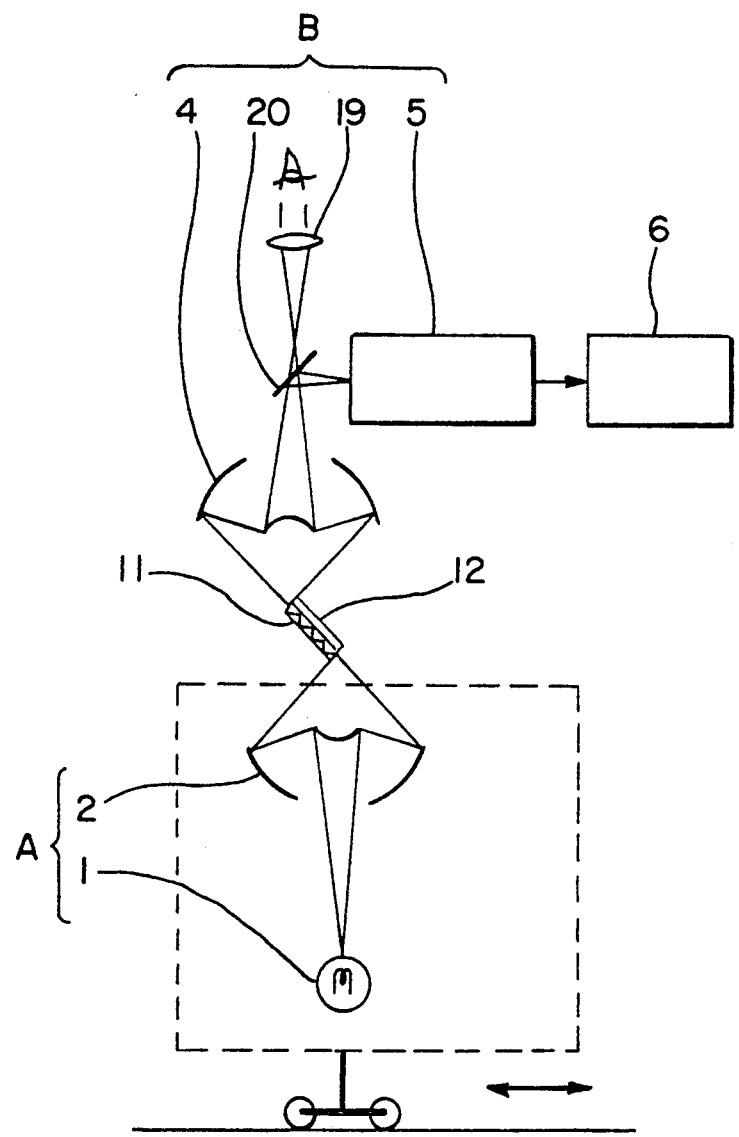
FIG. 2 is a cross-sectional depiction of an optical arrangement for ATR analysis conducted by the preferred embodiment of the invention.

FIGS. 1 and 2 illustrate a preferred embodiment of an infrared microscopic spectrometer according to the present invention. As shown, a collecting element (A) includes a light source 1 and a condenser mirror system 2. An analysis portion (B) includes an object mirror system 4, a spectrometric system 5, an eyepiece 19, and an optical path changing mirror 20.

Also included within the infrared microscopic spectrometer according to the preferred embodiment of the present invention is a moving means (C) for slidably shifting the collecting element (A) in a direction perpendicular with a transmissive optical axis through the sample 3. The moving mechanism (C) can either manually or automatically slidably shift the collecting element (A) in a direction shown by arrows 21 to provide an optional change of the optical path between the collecting element (A) and the analysis portion (B). The moving mechanism (C) may include a marking or other memory system for accurately remembering the positions of the different optical paths, i.e., for transmissive analysis and for ATR analysis. Furthermore, a limit switch may be used to improve reproductivity when the moving means (C) is driven by a motor.

Figure 3:
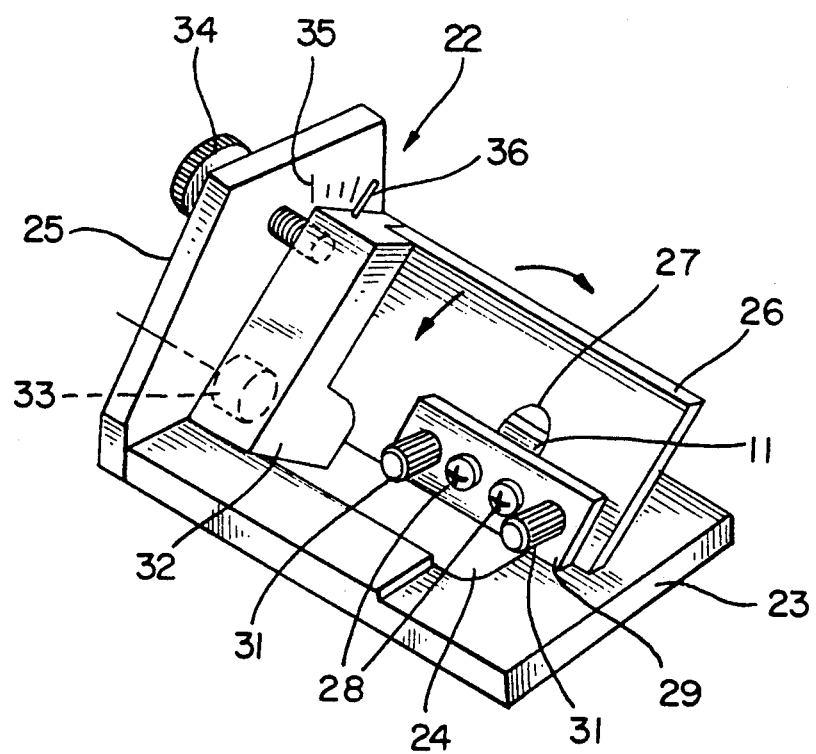
FIG. 3 is a perspective view showing one example of a holding device for an ATR crystal.
Figure 4:
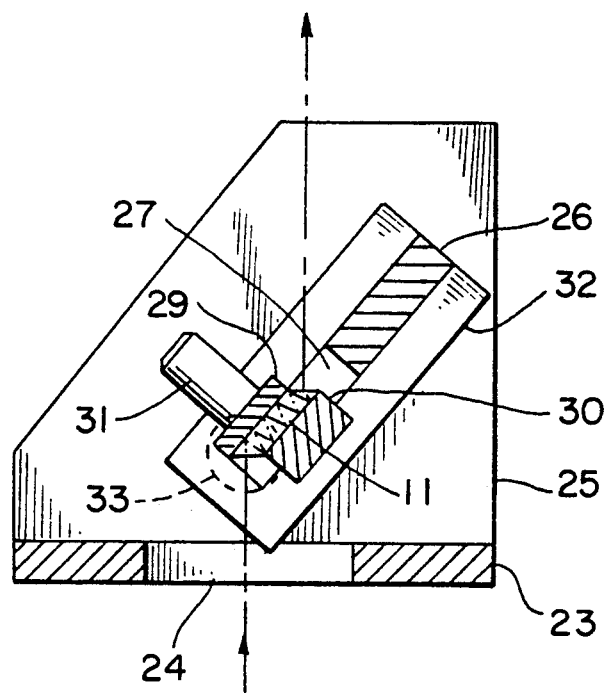
FIG. 4 is a longitudinal sectional view showing the holding device of FIG. 3.

The preferred embodiment of the invention also includes a holding device 22 for the ATR crystal 11. The holding device is shown in FIGS. 3 and 4. The holding device is placed on a stage (not shown) arranged between the collecting element (A) and the analysis portion (B).

As shown in FIGS. 3 and 4, a base plate 23 of the holding device is provided with a light incident hole 24 for allowing light from a light source, 1 to be incident upon the ATR crystal 11 through the base plate 23. A sample holder 26, which may be made from aluminum, is adapted to be rotatable along a shaft provided on the lower side of side plate 25. The sample holder 26 is provided with a holding opening 27 on its lower side facing the light incident hole 24.

The ATR crystal 11 which may be used in this preferred embodiment has a preferred size of 1 mm thick × 10 mm long × 5 mm wide to provide for a sample which may have the size of 500 $\mu m \times 500$ $\mu m$.

Two crystal setscrews 28 may be screwed into the sample holder 26. A sample counter member 29 has a plate-like shape and is provided with through-holes (not shown) which allow a head portion of a crystal setscrew 28 and a counter member setscrew 31 to be passed, respectively. A second sample counter member 30 is provided with a projection (not shown) having a height almost one-half the thickness of the sample holder 26 and a tapped hole (not shown), which allows a counter member setscrew 31 to screwingly mate therewith.

The ATR crystal 11 and the sample 12 are placed in the sample holder 26 as follows: First, the ATR crystal 11 is inserted into the holding opening 27, and then fixed in the sample holder 26 by the crystal setscrews 28. Thereafter, the sample 12 is adhesively held between both surfaces in a direction of the thickness of the ATR crystal 11 at a position close to the light incident hole 24. The sample counter members 29 and 30 are placed on both surfaces of the sample holder 26 to place the sample 12 between the ATR crystal 11 and the sample counter members 29 and 30. The counter member setscrew 31, passed through from the side of the sample counter member 29, is tightened, thereby fixing the sample 12 in place, adhering closely to the ATR crystal 11.

The sample holder 26 is rotatably constructed. The sample holder 26 is provided with a block portion 32 which is pivoted on a horizontal shaft 33 provided below the side plate 25. The side plate 25 is also provided with a circular guide groove (not shown), with said horizontal shaft 33 as a center above the guide groove. The block portion 32 is provided with a tapped hole (not shown) on the side of the side plate 25 which fits within the guide groove.

The sample holder 26 is positionally fixed by passing the guide groove from an outer side of the side plate 25 and tightening holder-fixing screw 34 screwed into the tapped hole. The sample holder 26 may be rotated with the shaft 33 as a center by loosening the holder-fixing screw 34 when an angle of incidence upon the ATR crystal 11 is changed. In the preferred embodiment, the sample holder 26 may rotate by 30 to 60 degrees.

An angle of incidence display scale 35 is also included in order to express an angle of incidence of infrared rays upon the ATR crystal. The display scale 35 is provided on the inside of the upper side of the side plate 25, whereby an angle of incidence display pin 36 arising from the upper end of the block portion 32, may be used to determine the angle of incidence of the infrared rays.

Focal positions of the condenser mirror system and the object mirror system 4 may be regulated by an up and down movement of the stage or of the condenser mirror system 2. These focal positions may also be aligned to agree with the end face of the ATR crystal 11, using visible light of a microscope as a standard.

The operation of the infrared microscopic spectrometer of the preferred embodiment of the present invention will now be described. As shown in FIG. 1, the optical path changing over mirror 20 is removed from the optical path in order to focus the system using visible light from the light source 1 and to observe the sample 3 through the eyepiece 19. Once the proper focal alignment is made, the light source 1 is changed to provide infrared rays, and the infrared rays are incident upon the sample 3 through the condenser mirror system 2. The optical path change mirror 20 is again disposed between the object mirror system 4 and the eyepiece 19 to focus the transmitted light from the object mirror system 4 into the spectrometric system 5. The spectrometric system 5 thereby provides a spectrum which may be displayed on display device 6, as shown in FIG. 1.

When the ATR analysis is to be conducted, the collecting element (A) is moved by moving mechanism (C) to provide a shift in the optical path between the infrared rays incident upon the ATR crystal 11 and the incident rays emitted from the ATR crystal 11. This shift may be seen in FIG. 2. Therein, the optical path change mirror 20 may be removed from the optical path to allow visible light from the light source 1 to be used to align the system. In this manner, the holder-fixing screw 34 (shown in FIGS. 3 and 4) is loosened, and the sample holder 26 is rotated to provide an angle of incidence of the ray incident upon the ATR crystal 11. Once this angle of incidence is aligned, the holder-fixing screw 34 may again be tightened. Additionally, the sample holder may be raised or lowered to provide the proper focal alignment for the system.

Once the optical path is regulated as described, the light source 1 is again changed to infrared rays, and the optical path changing.. over mirror 20 is again disposed between the object mirror system 4 and the eyepiece 19 to provide an optical path for the infrared rays through the ATR crystal 11 and into the spectrometric system 5 to allow for an analysis.

As can be understood from FIGS. 3 and 4, the sample holder 26 allows the angle of incidence of the ATR crystal to be continuously changed and rotated, and thus the position of the emitting side of the ATR crystal 11 can be regulated at a shift distance of the optical axes for every angle selected. Consequently, the sample holder 26 holding the ATR crystal 11 and the object mirror system 4 can be simultaneously moved while holding a distance between them constant. Furthermore, the difference in the shift between the optical axes due to a difference in the angle of incidence can be compensated for by moving the collecting element portion (A) with the moving mechanism (C).

Figure 5:
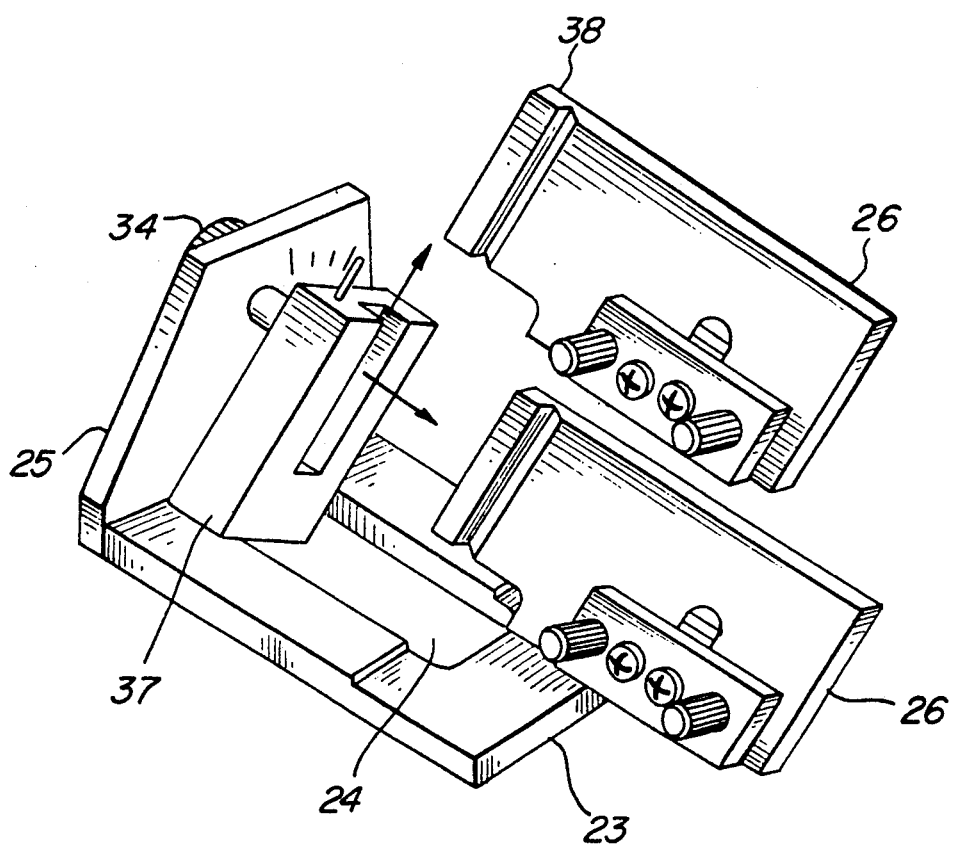
FIG. 5 is a perspective view showing a second preferred embodiment of a holding device for an ATR crystal.
Figure 6:
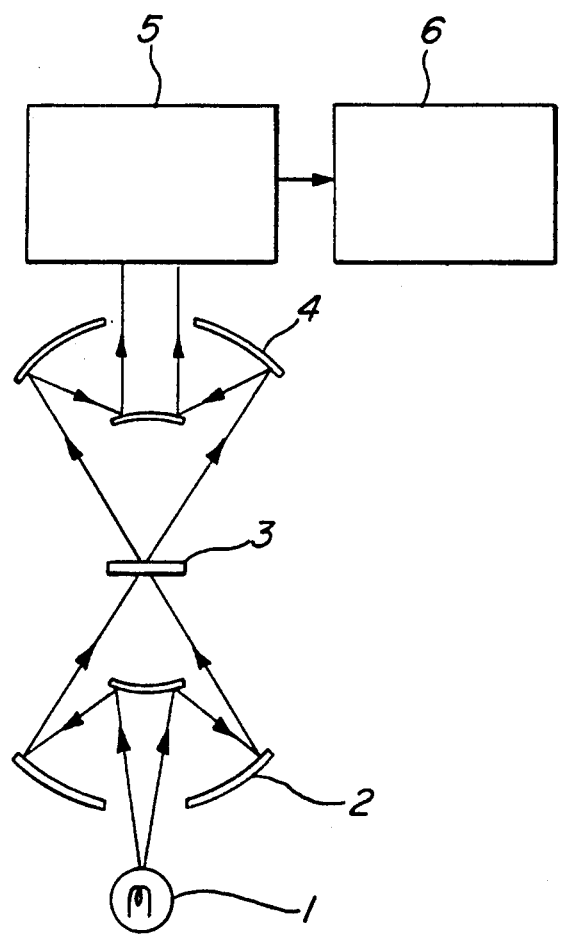
FIG. 6 is a cross-sectional block diagram showing a conventional transmission infrared microscopic spectrometer.
Figure 7:
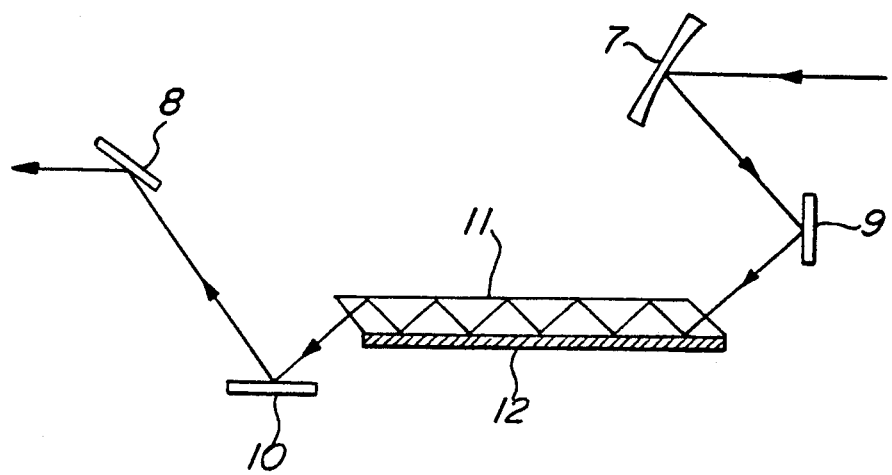
FIG. 7 is a cross-sectional diagram showing ATR analysis.
Figure 8:
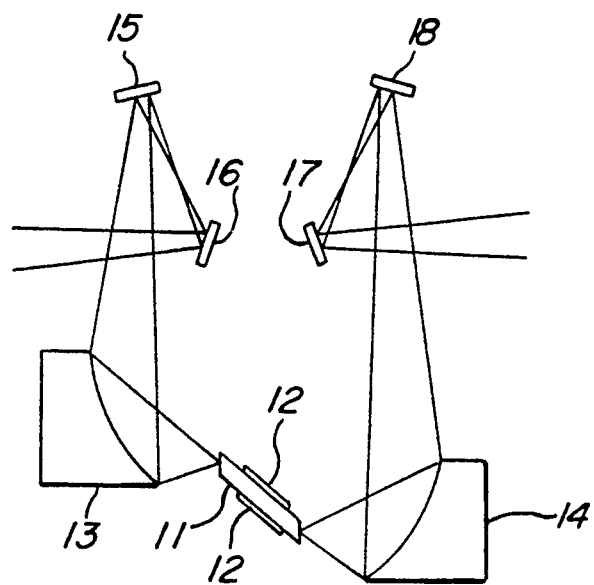
FIG. 8 is a cross-sectional block diagram showing ATR analysis for use by an infrared microscopic spectrometer.

A further embodiment of the sample holding mechanism 26 is shown in FIG. 5. In the embodiment shown in FIG. 5, the sample holder 26 may be separated from the side plate 25. Side plate 25 is provided with a holder fitting portion 37 rotatable in the same manner as the block portion 32 in the embodiment of FIGS. 3 and 4. The end portion 38 of the sample holder 26 is inserted into the holder fitting portion 37 so as to detachably hold the sample holder 26.

If a bowl plunger is used as the holder fitting portion 37, no shift is generated in the optical axes and the angle of incidence. Thus the sample holder 26 can be removed and realigned with excellent reproducibility.

In operation, the ATR crystal may also be rotated using the emitting portion of the ATR crystal 11 as the center of rotation, and the analysis portion may also be slidably moved in place of the movement of the collecting element. Furthermore, it is to be understood that the sample is not to be limited in size to that discussed in the Description of the Preferred Embodiment and, although the described embodiments relate to transmission-type infrared microscopic spectrometers, the present invention can also be applied to reflection-type infrared microscopic spectrometers.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

We claim:

1. An infrared microscopic spectrometer, comprising:
   a collecting element for focussing infrared rays upon a sample;
   an analysis portion for receiving affected infrared rays from the sample and spectrometrically analyzing the affected rays; and
   a moving means for shifting the collecting element with respect to the analysis portion between a first position allowing the sample to be analyzed transmissively using infrared spectroscopy and a second position allowing the sample to be tested by ATR analysis, wherein the first position provides a single optical axis aligning the collecting element and the analysis portion for allowing the sample to be transmissively tested, the moving means shifting the collecting element along a direction perpendicular to the single optical axis of the first position to provide an optical path for the second position, the optical path of the second position allowing the infrared rays to travel through an ATR crystal.

2. The infrared microscope spectrometer of claim 1, wherein the collecting element includes a light source emitting infrared rays and a condenser mirror system for collecting the infrared rays and focussing the infrared rays upon the sample.

3. The infrared microscope spectrometer of claim 1, wherein the analysis portion includes an object mirror system for receiving the affected infrared rays and enlargedly focussing the affected infrared rays upon a spectrometer system for analysis.

4. The infrared microscope spectrometer of claim 1, further comprising a sample holding structure for holding a sample adjacent an ATR crystal, the sample holding structure being placed within a optical path between the collecting element and the analysis portion.

5. The infrared microscope spectrometer of claim 4, wherein the sample holding structure allows the ATR crystal and the sample to be rotatable to provide proper alignment of the ATR crystal within the optical path.

6. The infrared microscope spectrometer of claim 5, wherein the sample holding structure further includes an angle of incidence display means for displaying an angle of incidence of the infrared rays upon the ATR crystal.

7. The infrared microscope spectrometer of claim 4, wherein the sample holding structure is movable along the optical path to provide correct focal distances between the collecting element, the ATR crystal and the analysis portion.

8. The infrared microscope spectrometer of claim 4, wherein the sample holding structure includes a sample holder holding the sample and the ATR crystal, the sample holder being detachably mounted within the sample holding structure in a controlled position to allow the sample holder to be replaced without misaligning the optical path.

9. An infrared microscopic spectrometer, comprising:
   a collecting element for focussing infrared rays upon a sample, the collecting element including a light source emitting infrared rays and a condenser mirror system for collecting the infrared rays and focussing the infrared rays upon the sample;
   an analysis portion for receiving affected infrared rays from the sample and spectrometrically analyzing the affected rays, the analysis portion including an object mirror system for receiving the affected infrared rays and enlargedly focussing the affected infrared rays upon a spectrometer system for analysis; and a moving means for shifting the collecting element with respect to the analysis portion between a first position allowing the sample to be analyzed transmissively using infrared spectroscopy and a second position allowing the sample to be tested by ATR analysis, the first position providing an optical axis aligning the collecting element and the analysis portion for allowing the sample to be transmissively tested, the moving means shifting the collecting element along a direction perpendicular to the optical axis of the first position to provide an optical path for the second position, the optical path of the second position allowing the infrared rays to travel through an ATR crystal; and a sample holding structure for holding the sample adjacent the ATR crystal, the sample holding structure being placed within the optical path of the second position between the collecting element and the analysis portion, the sample holding structure allowing the ATR crystal and the sample to be rotatable to provide proper alignment of the ATR crystal within the optical path, the sample holding structure being movable along the optical path to provide correct focal distances between the collecting element, the ATR crystal and the analysis portion and wherein the sample holding structure further includes an angle of incidence display means for displaying an angle of incidence of the infrared rays upon the ATR crystal.

* * * * *